(12) United States Patent
Shitagaki et al.

(10) Patent No.: US 7,355,340 B2
(45) Date of Patent: Apr. 8, 2008

(54) QUINOXALINE DERIVATIVES, ORGANIC SEMICONDUCTOR DEVICE AND ELECTROLUMINESCENT DEVICE

(75) Inventors: Satoko Shitagaki, Kanagawa (JP); Hiroko Yamazaki, Kanagawa (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 205 days.

(21) Appl. No.: 10/706,291

(22) Filed: Nov. 13, 2003

(65) Prior Publication Data

US 2005/0003232 A1 Jan. 6, 2005

(30) Foreign Application Priority Data

Nov. 13, 2002 (JP) ............................. 2002-329251

(51) Int. Cl.
*H01L 51/54* (2006.01)
*C09K 11/06* (2006.01)

(52) U.S. Cl. .................. 313/504; 428/690; 428/917; 257/40; 257/E51.05; 544/343; 544/344

(58) Field of Classification Search ................ None
See application file for complete search history.

(56) References Cited

U.S. PATENT DOCUMENTS

| | | | |
|---|---|---|---|
| 3,765,898 A | 10/1973 | Bauer et al. | |
| 4,286,479 A | 9/1981 | Baumann et al. | |
| 6,482,949 B1 | 11/2002 | Sessler et al. | |
| 6,723,445 B2 * | 4/2004 | Li et al. | 428/690 |
| 2003/0162960 A1 | 8/2003 | Sessler et al. | |

FOREIGN PATENT DOCUMENTS

| | | |
|---|---|---|
| CH | 599569 | 5/1978 |
| JP | 54 005293 | 1/1979 |
| JP | 64 057261 | 3/1989 |
| JP | 64 063971 | 3/1989 |
| JP | 05 222181 | 8/1993 |
| JP | 06-207169 | 7/1994 |
| JP | 07-026255 | 1/1995 |
| JP | 09-013025 | 1/1997 |
| JP | 09 188874 | 7/1997 |
| JP | 2003 040873 | 2/2003 |
| WO | WO 02/94796 A2 | 11/2002 |

OTHER PUBLICATIONS

Machine-assisted translation of JP 09-188874.*
Accession No. 1997:491099 HCAPLUS (for JP 09-188874).*
Machine translation of JP 2003-040873 (Feb. 2003).*
C.W. Tang et al.; "Organic electroluminescent diodes"; *Applied Physics Letters* 51(12); pp. 913-915; Sep. 21, 1987.
Yasunori Kijima et al.; "A Blue Organic Light Emitting Diode"; *Japan Journal of Applied Physics* 38(1)(9A); pp. 5274-5277; Sep. 1999.
D.F. O'Brien et al.; "Improved energy transfer in electrophosphorescent devices"; *Applied Physics Letters* 74(3); pp. 442-444; Jan. 18, 1999.
Hosokawa, Chishio, "Development of Low Molecular Red Light-Emitting Materials with Long Life time", *Idemitsu Kosan Co., Ltd./Central Research Laboratory*, pp. 3-1 to 3-12, Apr. 10, 2002, (full translation).
International Application No. PCT/JP03/13764 Search and Examination Report dated Dec. 9, 2003.
Alkhathlan, et al., "Spectroscopic Studies of Benzimidazole, Quinoxaline and Quinoline Derivatives", *Journal of Chemical Research Synopses*, No. 1, pp. 10-11 (1995).
Alkhathlan, et al., "Spectroscopic Studies of Benzimidazole, Quinoxaline and Quinoline Derivatives", *Journal of Chemical Research (M)*, pp. 201-220 (1995).
Chemical Abstract, vol. 55; pp. 1961-1962 (19934I-19935A-C).
Cohen, et al., "New Polyheterocyclic 4nπ-Electron Dianions: Paratropicity, Charge Delocalization, and Reactions", *Journal of the American Chemical Society*, vol. 108/No. 22, pp. 7039-7044 (1986).
Guldi, et al., "Intramolecular Energy Transfer in Fullerene Pyrazine Dyads", *Journal of Physical Chemistry A*, vol. 102/No. 48, pp. 9679-9685 (1998).
Schürmann, et al., "Ultraviolet Photoelectron Spectroscopic Study of Heterocyclic Model Compounds for Electroluminescent Devices", *Synthetic Metals*, vol. 102, pp. 1069-1070 (1999).

* cited by examiner

*Primary Examiner*—Marie Yamnitzky
(74) *Attorney, Agent, or Firm*—Fish & Richardson P.C.

(57) ABSTRACT

The present invention is to provide quinoxaline derivatives, which have excellent electron transportation and hole blocking properties, and which can be formed into a film without being crystallized. According to the invention, quinoxaline derivatives represented by the general [formula 1] are synthesized.

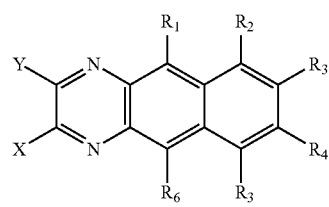

[formula 1]

(wherein X and Y represent a substituted or unsubstituted aryl group, or a substituted or unsubstituted heterocyclic group, and R1 to R6 represent individually hydrogen, an alkyl group, an alkoxyl group, a substituted or unsubstituted aryl group, and a substituted or unsubstituted heterocyclic group. Further, an organic semiconductor device including an electroluminescent device containing the foregoing quinoxaline derivatives is formed.)

17 Claims, 7 Drawing Sheets

QUINOXALINE DERIVATIVES, ORGANIC SEMICONDUCTOR DEVICE AND ELECTROLUMINESCENT DEVICE

TECHNICAL FIELD

The present invention relates to quinoxaline derivatives used as an organic semiconductor material; an organic semiconductor device containing the quinoxaline derivative; and an electroluminescent device containing the quinoxaline derivative.

BACKGROUND ART

Organic compounds have various material series compared with inorganic compounds, and so there is a possibility that various functional materials can be synthesized by an appropriate molecular design. In addition, a formation of organic compounds, for example, a film has excellent flexibility, and becomes adequately workable by polymerization. Therefore, photonics and electronics, each of which is formed by functional organic materials, have attracted attention in recent years.

For example, as an example of photoelectronics using organic semiconductor materials as functional organic materials: a solar battery or an electroluminescent device (also referred to as an organic electroluminescent device) is nominated. These devices utilize electrical properties (carrier transportation properties) and photophysical properties (light absorption or light emission properties) of organic semiconductor materials. Above all, an electroluminescent device has achieved remarkable development.

The basic structure of an electroluminescent device was provided by C. W. Tang et al. in 1987. The device, which is one type of a diode, has the structure composed of an organic thin film with an overall thickness of approximately 100 nm formed by stacking layers of organic compounds having hole transportation properties and organic compounds having electron transportation properties, and a pair of electrodes interposing the organic thin film. Light emission can be observed from the compounds having electron transportation properties formed by light-emitting materials (phosphorescent materials) by applying voltage to the device. (For example, refer to C. W. Tang and S. A. Vanslyke, "Organic electroluminescent diodes", Applied Physics Letters, Vol.51, No.12, 913-915 (1987) [Reference 1].)

Hereby, the combination of hole transporting materials and an electron transporting materials is essential for the device containing organic semiconductor materials, especially, a solar battery or an electroluminescent device which employs heterojunction.

However, hole transporting materials account potentially for a large share of organic semiconductor materials in general. With respect to the absolute value of the carrier mobility, the hole mobility of hole transporting materials is several orders of magnitude larger than the electron mobility of electron transporting materials. Therefore, electron transporting materials having excellent electron transportation properties have been hoped.

Further, as electron transporting materials, it has been reported that quinoxaline derivatives which are known as having electron transportation properties are binary-quantificated to improve the thermal physical properties. (For example, refer to Unexamined Patent Publication No. 6-207169 [Reference 2].)

However, electron transportation properties are deteriorated by the binary quantification since interaction of molecules is weakened. In addition, physical properties such as the energy gaps of the quinoxaline derivatives are diverged largely from those of original quinoxaline derivatives.

It has also been disclosed that thermal physical properties (glass transition point or melting point) are improved by introducing a condensed ring into a quinoxaline skeleton to form an adamant plane structure. (For example, refer to Unexamined Patent Publication No. 9-13025 [Reference 3].)

However, although the materials have high thermal physical properties, the materials have demerit of being difficult in maintaining amorphous state and being susceptible to be crystallized.

In addition, as electron transporting materials, materials having hole blocking properties, (which is referred to as hole blocking material especially in this case) are known. In this instance, wide ranging applications become possible since the hole blocking material has a function of blocking holes in addition to a function of transporting electrons. For example, it has been reported that, by interposing a hole blocking material between a hole transporting layer and an electron transporting layer, holes are trapped into the hole transporting layer, and carriers in the hole transporting layer are selectively recombined, then light is generated in an electroluminescent device. (For example, refer to Yasunori KUIMA, Nobutoshi ASAI and Shin-ichiro TAMURA, "A Blue Organic Light Emitting Diode", Japanese Journal of Applied Physics, vol. 38, 5274-5277 (1999) [Reference 4])

In addition, it has been reported that high efficient light emission can be obtained by using hole blocking materials for forming a triplet light-emitting device. (For example, refer to D. F. O'Brien, M. A. Baldo, M. E. Thompson and S. R. Forrest, "Improved energy transfer in electrophosphorescent devices", Applied Physics Letters, vol. 74, No. 3, 442-444 (1999) [Reference 5].)

Though a triplet light-emitting device is an effective art for a high efficient electroluminescent device, the electroluminescent device cannot generate light efficiently without using a hole blocking material. Consequently, the hole blocking material becomes an important key.

Hence, hole blocking materials have great importance among an electron transporting material; however, the kinds of materials having both excellent electron transportation properties and excellent hole blocking properties are strictly limited in the present situation. As one of a few examples, BCP (bathocuproin) can be used, which is used in References 4 and 5. However, the BCP deposited film is susceptible to be crystallized, and has significantly adverse effects on the reliability of devices in case of utilizing the BCP for devices actually.

Therefore, among an electron transporting material, a hole blocking material which has excellent hole blocking properties, has excellent film quality, and is hardly crystallized has been hoped.

DISCLOSURE OF INVENTION

[Problem to be Solved by the Invention]

It is an object of the present invention to provide quinoxaline derivatives, which has excellent electron transportation and hole blocking properties, and which can be formed into a film without being crystallized. It is another object of the invention to provide an organic semiconductor device and an electroluminescent device which is one type of the organic semiconductor devices, each of which has high efficiency and high driving stability by forming the organic semiconductor device and the electroluminescent device by the foregoing quinoxaline derivatives.

[How to Solve the Problems]

One aspect of the present invention is to provide the following quinoxaline derivatives denoted by reference numerals (1), (2), (3), (4), (5), and (6).

(1) Quinoxaline derivatives represented by general [formula 1]:

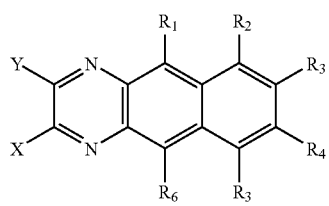

[formula 1]

(wherein X and Y represent an alkyl group, a substituted or unsubstituted aryl group, or a substituted or unsubstituted heterocyclic group, and R1 to R6 represent individually hydrogen, an alkyl group, an alkoxyl group, a substituted or unsubstituted aryl group, and a substituted or unsubstituted heterocyclic group.)

(2) Quinoxaline derivatives represented by general [formula 2]:

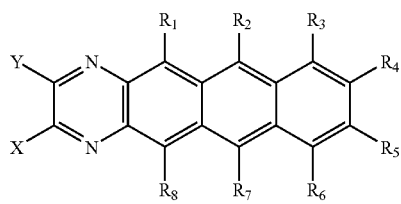

[formula 2]

(wherein X and Y represent an alkyl group, a substituted or unsubstituted aryl group, or a substituted or unsubstituted heterocyclic group, and R1 to R8 represent individually hydrogen, an alkyl group, an alkoxyl group, a substituted or unsubstituted aryl group, and a substituted or unsubstituted heterocyclic group.)

(3) Quinoxaline derivatives represented by general [formula 3]:

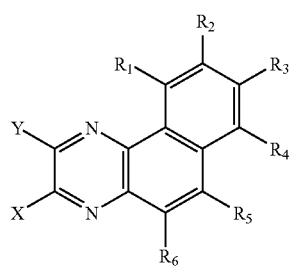

[formula 3]

(wherein X and Y represent an alkyl group, a substituted or unsubstituted aryl group, or a substituted or unsubstituted heterocyclic group, and R1 to R6 represent individually hydrogen, an alkyl group, an alkoxyl group, a substituted or unsubstituted aryl group, and a substituted or unsubstituted heterocyclic group.)

(4) Quinoxaline derivatives represented by general [formula 4]:

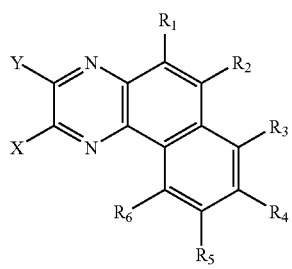

[formula 4]

(wherein X and Y represent an alkyl group, a substituted or unsubstituted aryl group, or a substituted or unsubstituted heterocyclic group, and R1 to R6 represent individually hydrogen, an alkyl group, an alkoxyl group, a substituted or unsubstituted aryl group, and a substituted or unsubstituted heterocyclic group.)

(5) Quinoxaline derivatives represented by general [formula 5]:

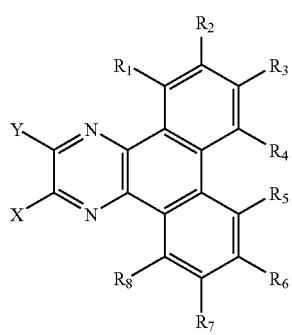

[formula 5]

(wherein X and Y represent an alkyl group, a substituted or unsubstituted aryl group, or a substituted or unsubstituted heterocyclic group, and R1 to R8 represent individually hydrogen, an alkyl group, an alkoxyl group, a substituted or unsubstituted aryl group, and a substituted or unsubstituted heterocyclic group.)

(6) Quinoxaline derivatives according to any one of (1) to (5), wherein quinoxaline derivatives including the heterocyclic group represented by general [formula 6]:

[formula 6]

(wherein A represents S or O.)

The quinoxaline derivatives according to the invention represented by the above (1) to (6) can be synthesized by using diketone and diamine as materials. The synthesis method for the quinoxaline derivatives (FuQn) according to the invention is not limited to the following synthesis method. A synthesis scheme of the quinoxaline derivatives represented by (5) is represented by way of an example:

[formula 7]

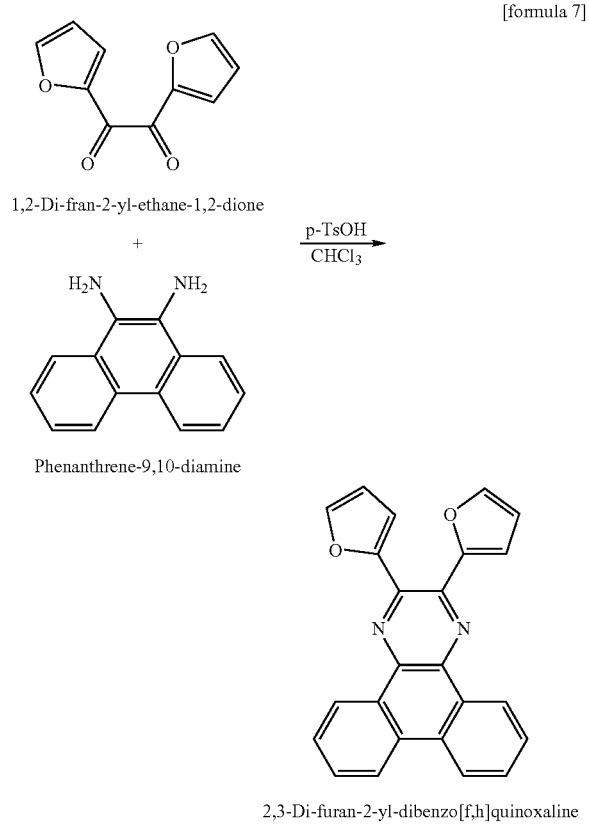

1,2-Di-fran-2-yl-ethane-1,2-dione

Phenanthrene-9,10-diamine 2,3-Di-furan-2-yl-dibenzo[f,h]quinoxaline

Specifically, diketone and diamine are dissolved into solvent such as chloroform (dehydrated chloroform), alcohol (methanol, ethanol, propanol, butanol), or the like, and the mixture is stirred and refluxed. In the middle of the reflux, para-toluenesulfonic acid is added, and the mixture is further stirred and refluxed. The reaction time is preferably from 1 to 24 hours.

In addition, with respect to each the above structure of quinoxaline derivatives, X and Y are an alkyl group, a substituted or unsubstituted aryl group, or a substituted or unsubstituted heterocyclic group. The quinoxaline derivatives have no plane structure, and so maintain an amorphous state at the state of forming a film to prevent crystallization. Therefore, the above quinoxaline derivatives have excellent film formation properties compared with the quinoxaline derivatives in which X and Y, which are disclosed in Reference 3 explained in background art, have ring structures.

Further, electron transportation properties can be improved since electric charges are polarized in case that X and Y have the above described structure. In addition, heterocyclic group is preferably included in order to improve electron transportation properties.

In another aspect, the invention relates to an organic semiconductor device including an electroluminescent device using quinoxaline derivatives in the above structures ((1) to (6)).

In another more aspect, the invention relates to an electroluminescent device using the quinoxaline derivatives as electron transporting materials by taking advantages that the quinoxaline derivatives in the above structures ((1) to (6)) have excellent electron transportation properties.

In further another more aspect, the invention relates to an electroluminescent device having a light-emitting layer which contains a quinoxaline derivative in the above structures ((1) to (6)) and a guest material. The quinoxaline derivatives according to the invention can form a light-emitting layer by using as a host material with another guest material since the quinoxaline derivatives have wide energy gaps.

In addition, the quinoxaline derivatives according to the invention is especially preferable in case of using phosphorescent materials as a guest materials which requires host material to have wide energy gaps.

The quinoxaline derivatives according to the invention can be used as a guest material for blue light emission since the quinoxaline derivatives according to the invention have wide energy gap and have a fluorescent wavelength around 450 nm. The quinoxaline derivatives according to the invention is a material that have electron transportation properties and are effective for reducing a driver voltage since it is generally known that membrane resistance can be reduced by using a material having electron transportation properties as a guest material.

In further additional aspect, the invention relates to an electroluminescent device using quinoxaline derivatives in the above structures ((1) to (6)) as hole blocking materials since the quinoxaline derivatives have excellent hole blocking properties.

Since the quinoxaline derivatives according to the invention have wide energy gaps, the electroluminescent device according to the invention preferably has a light-emitting layer containing phosphorescent materials which are required wide energy gap in case of using the quinoxaline derivatives for a hole blocking layer as a hole blocking material.

[Advantage of Invention]

According to the invention, quinoxaline derivatives which have excellent electron transporting properties and hole blocking properties, and which can be formed into a film without being crystallized can be obtained. Accordingly, organic semiconductor device and electroluminescent device, each of which has high efficiency and high driving stability can be provided by manufacturing the organic semiconductor device and the electroluminescent device which is one type of the organic semiconductor device by the above quinoxaline derivatives.

BEST MODE FOR CARRYING OUT THE INVENTION

Figure 1:
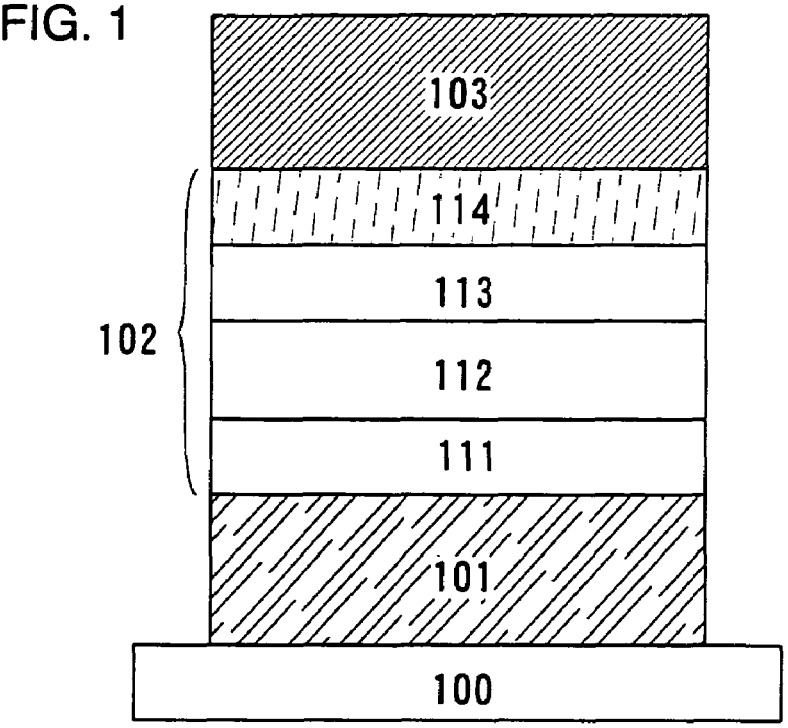
FIG. 1 is an explanatory view of a configuration of an electroluminescent device according to the invention.

The structure of an electroluminescent device according to the invention has basically an electroluminescent layer (a hole injecting layer, a hole transporting layer, a light-emitting layer, a blocking layer, an electron transporting layer, and an electron injecting layer) containing the above mentioned quinoxaline derivatives in the above structures ((1) to (6)) between a pair of electrodes (an anode and a cathode). For instance, the electroluminescent device having the following structure: anode/hole injecting layer/light-emitting layer/electron transporting layer/cathode, anode/hole injecting layer/hole transporting layer/light-emitting layer/electron transporting layer/cathode, anode/hole injecting layer/hole transporting layer/light-emitting layer/electron transporting layer/electron injecting layer/cathode, anode/hole injecting layer/hole transporting layer/light-emitting layer/hole blocking layer/electron transporting layer/cathode, anode/hole injecting layer/hole transporting layer/light-emitting layer/hole blocking layer/electron transporting layer/electron injecting layer/cathode, or the like, the quinoxaline derivatives can be used for the electron transporting layer, the blocking layer, or the light-emitting layer.

In addition, the electroluminescent device according to the invention is preferably supported by a substrate. The substrate is not especially limited, any substrate used for the conventional electroluminescent device can be used, for example, a glass substrate, a quartz substrate, a transparent plastic substrate.

As an anode material for the electroluminescent device according to the invention, metals having a large work function (at least 4.0 eV), alloys, electric conductive compounds, or a mixture of the above materials are preferably used. As a specific example of an anode material, in addition to ITO (indium tin oxide), IZO (indium zinc oxide) which is a mixture of indium oxide and zinc oxide (ZnO) of from 2 to 20%; aurum (Au); platinum (Pt); nickel (Ni); tungsten (W); chromium (Cr); molybdenum (Mo); iron (Fe); cobalt (Co); copper (Cu); palladium (Pd); metal nitride (TiN); or the like can be used.

On the other hand, as cathode materials, metals having a small work function (at most 3.8 eV), alloys, electric conductive compounds, or a mixture of the above are preferably used. As a specific example of cathode materials, transition metals including rare earth metals can be used, in addition to elements belonging to a first group or a second group of the periodic table of the elements, that is, alkali metals such as Li or Cs, alkali earth metals such as Mg, Ca, Sr, alloys including the above elements (Mg:Ag, Al:Li), or compounds (LiF, CsF, CaF$_2$). In addition, the cathode can also be formed to have a lamination structure including metals (including alloys) such as Al, Ag, or ITO and the foregoing materials.

An anode or a cathode is formed by depositing the above described anode materials and cathode materials respectively by vapor deposition, sputtering, or the like, to form a thin film. The anode and cathode are preferably formed to have thicknesses of from 10 to 500 nm.

Within the electroluminescent device according to the invention, light resulted from the recombination of carriers in the electroluminescent layer is emitted to outside through either the anode or the cathode, or both of the electrodes to outside. Therefore the anode is formed by a transparent material in case of emitting light from the anode, and the cathode is formed by a transparent material in case of emitting light from the cathode.

In addition, a known low molecular weight material or a known high molecular weight material can be used for forming the electroluminescent layer. As materials for forming the light-emitting layer, materials composed of not only organic compound materials but also inorganic compound materials can be used.

The electroluminescent layer is formed by stacking, in combination, a hole injecting layer formed by a hole injecting material, a hole transporting layer formed by a hole transporting material, a light-emitting layer formed by a light-emitting material, a blocking layer formed by a blocking material, an electron transporting layer formed by an electron transporting material, an electron injecting layer formed by an electron injecting material, or the like.

In case of using quinoxaline derivatives for forming the electron transporting layer in the invention, the electroluminescent layer is formed by stacking at least the light-emitting layer by the anode side and the electron transporting layer containing quinoxaline derivatives by the cathode side. The other layers such as the hole injecting layer and the hole transporting layer can be stacked in combination as appropriate. Specific materials for forming the hole injecting layer and the hole transporting layer are explained hereinafter.

As hole injecting materials, porphyrin compounds are useful among organic compounds such as phthalocyanine (hereinafter, H$_2$-Pc), copper phthalocyanine (hereinafter, Cu-Pc), or the like. Further, chemical-doped conductive polymer compounds can be used, such as polyethylene dioxythiophene (hereinafter, PEDOT) doped with polystyrene sulfonate (hereinafter, PSS), or polyaniline, polyvinyl carbazole (PVK).

As hole transporting materials, aromatic amine (that is, the one having a benzene ring-nitrogen bond) compounds are preferably used. For example, in addition to the above-mentioned TPD, derivatives thereof such as 4,4'-bis[N-(1-naphthyl)-N-phenyl-amino]-biphenyl (hereinafter, α-NPD) is widely used. Also used are star burst aromatic amine compounds, including: 4,4',4"-tris(N,N-diphenyl-amino)-triphenyl amine (hereinafter, TDATA); and 4,4',4"-tris[N-(3-methylphenyl)-N-phenyl-amino]-triphenyl amine (hereinafter, MTDATA).

As light emitting materials, in specific, metal complexes such as tris(8-quinolinolato) aluminum (hereinafter, Alq$_3$), tris(4-methyl-8-quinolinolato) aluminum (hereinafter, Almq$_3$), bis(10-hydroxybenzo[h]-quinolinato) beryllium (hereinafter, BeBq$_2$), bis(2-methyl-8-quinolinolato)-(4-hydroxy-biphenylyl)-aluminum (hereinafter, BAlq), bis [2-(2-hydroxyphenyl)-benzooxazolato] zinc (hereinafter, Zn(BOX)$_2$), and bis [2-(2-hydroxyphenyl)-benzothiazolato] zinc (hereinafter, Zn(BTZ)$_2$). Also, fluorescent dyes are useful.

For forming the electron transporting layer containing quinoxaline derivatives, any one of the above mentioned quinoxaline derivatives ((1) to (6)) are used.

In the invention, in case of using quinoxaline derivatives as a host material for the light-emitting layer, the light-emitting layer is formed of at least quinoxaline derivatives as a host material and a light-emitting layer with a guest material. The other layers such as the hole injecting layer, the hole transporting layer, the electron transporting layer, and the blocking layer can be stacked in combination as appropriate. In this instance, the hole injecting layer and the hole transporting layer can be formed by the same quinoxaline derivatives as those used for forming the electron transporting layer.

As electron transporting materials, metal complexes having a quinoline skeleton or benzoquinoline skeleton, such as the aforementioned $Alq_3$, $Almq_3$, $BeBq_2$; and mixed ligand complexes such as Balq are useful. In addition, metal complexes having oxazole-based and thiazole-based ligands such as $Zn(BOX)_2$ and $Zn(BTZ)_2$ can be used. Further, oxadiazole derivatives such as 2-(4-biphenylyl)-5-(4-tert-butylphenyl)-1,3,4-oxadiazole (hereinafter, PBD), and 1,3-bis[5-(p-tert-butylphenyl)-1,3,4-oxadiazole-2-yl] benzene (hereinafter, OXD-7); triazole derivatives such as 3-(4-tert-butylphenyl)-4-phenyl-5-(4-biphenylyl)-1,2,4-triazole (hereinafter, TAZ) and 3-(4-tert-butylphenyl)-4-(4-ethylphenyl)-5-(4-biphenylyl)-1,2,4-triazole (hereinafter, p-EtTAZ); and phenanthroline derivatives such as bathophenanthroline (hereinafter, BPhen) and bathocuproin (hereinafter, BCP) can be used in addition to metal complexes.

As a blocking material, the above mentioned BAlq, OXD-7, TAZ, p-EtTAZ, BPhen, BCP, or the like can be used.

The light-emitting layer in this instance is formed by combining quinoxaline derivatives ((1) to (6)) as a host material and a guest material.

As a guest material for forming the light-emitting layer, a triplet light-emitting material (phosphorescent material) such as tris(2-phenylpyridine)iridium (hereinafter, $Ir(ppy)_3$), and 2,3,7,8,12,13,17,18-octaethyl-21H, 23H-porphyrin-platinum (hereinafter, PtOEP) can be used in addition to quinacridone, diethylquinacridone (DEQ), rubrene, perylene, DPT, Co-6, PMDFB, BTX, ABTX, DCM, DCJT.

On the other hand, quinoxaline derivatives can be used as a guest material for the electroluminescent layer in the invention. In this instance, the electroluminescent layer is formed of at least quinoxaline derivatives as a guest material and a electroluminescent layer with a host material. The other layers such as the hole injecting layer, the hole transporting layer, the electron transporting layer, and the blocking layer can be stacked in combination as appropriate. These materials can be the same as those described above.

Further, in case of using quinoxaline derivatives for the blocking layer in the invention, the electroluminescent layer is formed by stacking at least the light-emitting layer by the anode side and the blocking layer containing quinoxaline derivatives by the cathode side. The other layers such as the hole injecting layer, the hole transporting layer, and the electron transporting layer can be stacked in combination as appropriate. In this instance, the hole injecting layer and the hole transporting layer can be formed by the same quinoxaline derivatives as those used for forming the electron transporting layer. In addition, the electron transporting layer can be formed by the same quinoxaline derivatives used as a host material for the light-emitting layer.

In case of using quinoxaline derivatives for the blocking layer, a triplet light-emitting material is preferably used in addition to the materials which are described above as a light-emitting material. Platinum or complexes having iridium as central metals can be used. As the triplet light-emitting material, tris(2-phenylpyridine)iridium (hereinafter, $Ir(ppy)_3$), and 2,3,7,8,12,13,17,18-octaethyl-21H, 23H-porphyrin-platinum (hereinafter, PtOEP) can be nominated.

EXAMPLES

Hereinafter, the present invention will be explained with synthesis examples, examples, and comparative examples according to the invention, but not limited to these examples.

Synthesis Example 1

A synthesis example represented by [formula 7] will be explained in detail.

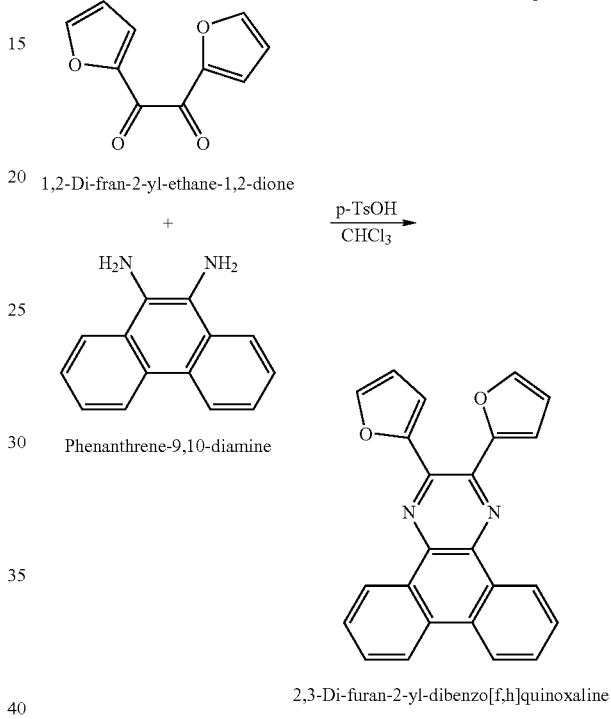

[formula 7]

1,2-Di-fran-2-yl-ethane-1,2-dione

Phenanthrene-9,10-diamine 2,3-Di-furan-2-yl-dibenzo[f,h]quinoxaline (Synthesis of 2,3-Di-furan-2-yl-dibenzo[f,h]quinoxaline)

Figure 9:
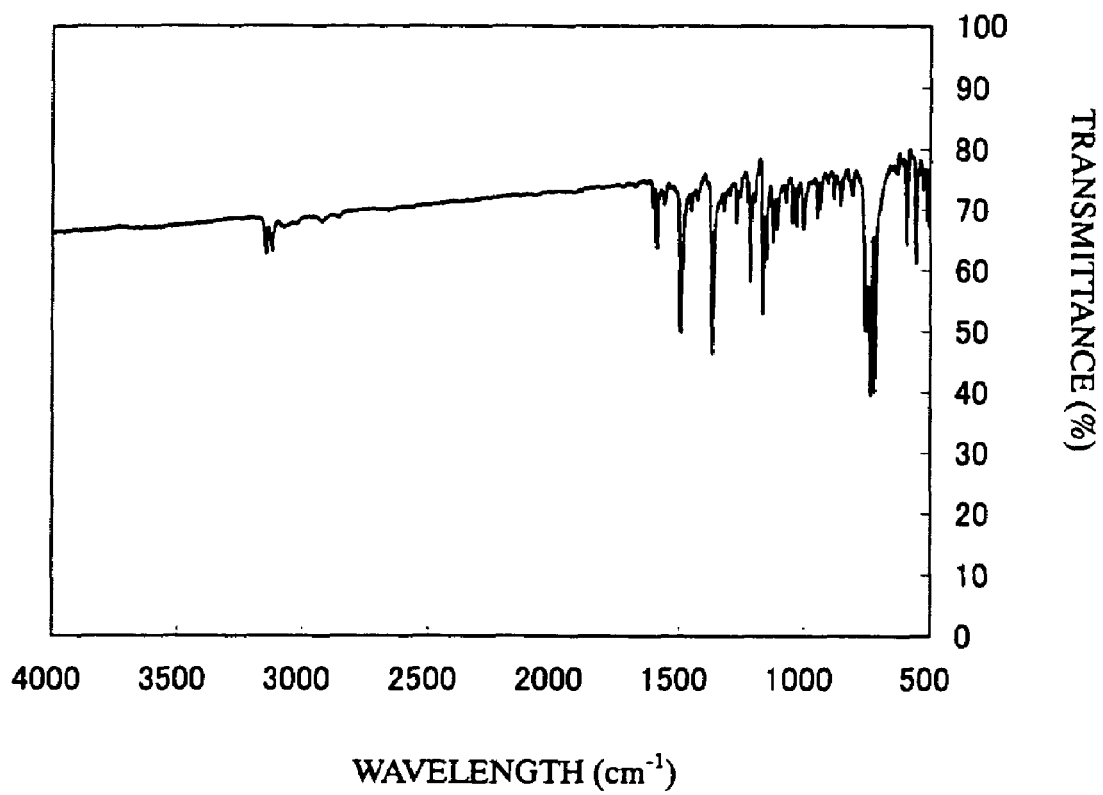
FIG. 9 is a graph showing IR spectrum of quinoxaline derivatives according to the invention.

In 1.90 g (10 mmol) of 1,2-Di-fran-2-yl-ethane-1,2-dione as diketone represented by reaction [formula 7] and 2.14 g (10 mol) of Phenanthrene-9,10-diamine as diamine, each of which was in a recovery flask, dehydrated chloroform (300 ml) was added. This obtained mixture was stirred and refluxed. After heating for 30 min., a spoonful of spatula of para-toluenesulfonic acid was added and the mixture was stirred and refluxed for 24 hours. After the reaction was completed, the reaction mixture was extracted with HClaq, $NaHCO_3$aq, and $H_2O$. $MgSO_4$ (anhydrous) was added to the obtained solution and the mixture was stirred all night. The solution was evaporated with an evaporator and dried under reduced-pressure at room temperature. The product was purified by column chromatography (developing solvent: toluene, Rf=0.80). After the column purification, yellow green powder was purified by sublimation to give pale yellow needle crystals. As a result of differential scanning calorimetric (DSC) analysis of the yellow pale needle crystals, melting point was 202° C. Further, as a result of infrared resonance spectrum measurement shown in FIG. 9, it can be considered that the reaction was advanced from the fact that each peak of vicinity of the absorption of from 3500 to 3300 cm$^{-1}$ derived from —$NH_2$ of an original material and vicinity of the absorption of 1680 cm$^{-1}$ derived from α-diketone was distinguished.

Figure 11:
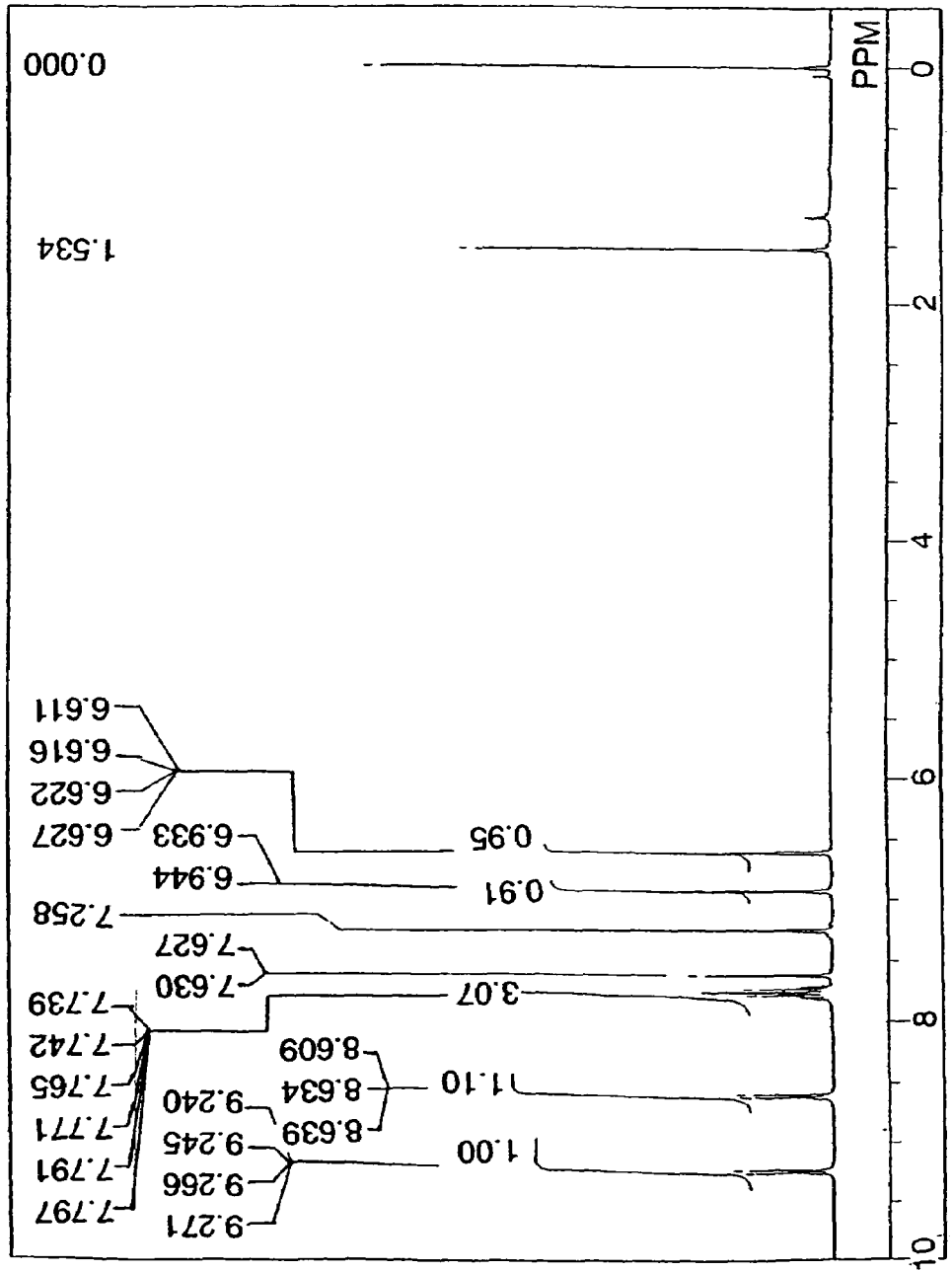
FIG. 11 is a $^1$H-NMR measurement result of quinoxaline derivatives according to the invention.

The obtained compounds were isolated and the isolated compounds were analyzed with ¹H-NMR. FIG. 11 is a measurement result. (Primary standard: TMS, solvent: chloroform, measurement wavelength: 400 MHz) σ (ppm)=6.61 (1H° 2-furan), 6.94(1H 2-furan), 7.63(1H 2 furan), 7.74-7.79(2H phenanthrene), 8.61-8.64 (1H phenanthrene), 9.24-9.28(1H phenanthrene). Hereby, 2,3-Di-furan-2-yl-dibenzo [f,h]quinoxaline having a construction represented by [formula 7] was recognized by the measurement result.

Synthesis Example 2

The reaction was carried out in accordance with the same procedures as those conducted in Synthesis Example 1 except that diketone shown in [formula 8] and diamine shown in [formula 9] were used. The obtained quinoxaline derivative is represented by [formula 10].

[formula 8]

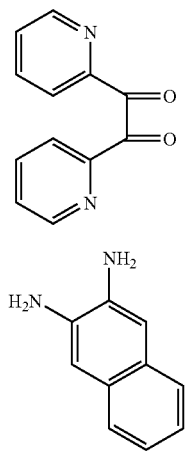

[formula 9]

[formula 10]

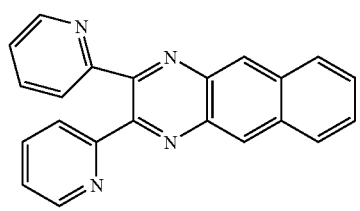

Synthesis Example 3

The reaction was carried out in accordance with the same procedures as those conducted in Synthesis Example 1 except that diketone shown in [formula 11] and diamine shown in [formula 12] were used. The obtained quinoxaline derivative is represented by [formula 13].

[formula 11]

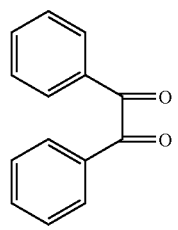

[formula 12]

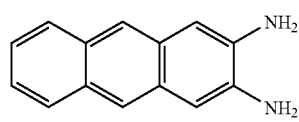

[formula 12]

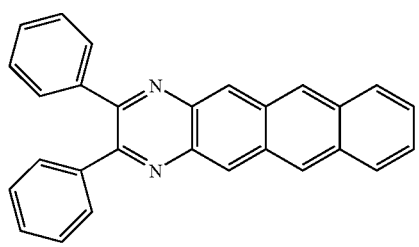

Synthesis Example 4

The reaction was carried out in accordance with the same procedures as those conducted in Synthesis Example 1 except that diketone shown in [formula 14] and diamine shown in [formula 15] were used. The obtained quinoxaline derivative is represented by [formula 16].

[formula 14]

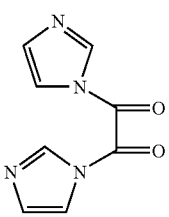

[formula 15]

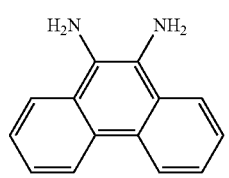

[formula 16]

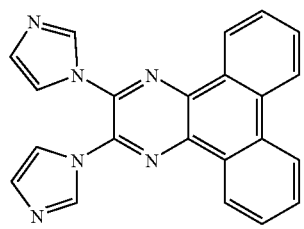

Synthesis Example 5

The reaction was carried out in accordance with the same procedures as those conducted in Synthesis Example 1 except that diketone shown in [formula 17] and diamine shown in [formula 9] were used. The obtained quinoxaline derivative is represented by [formula 18].

[formula 17]

[formula 9]

[formula 18]

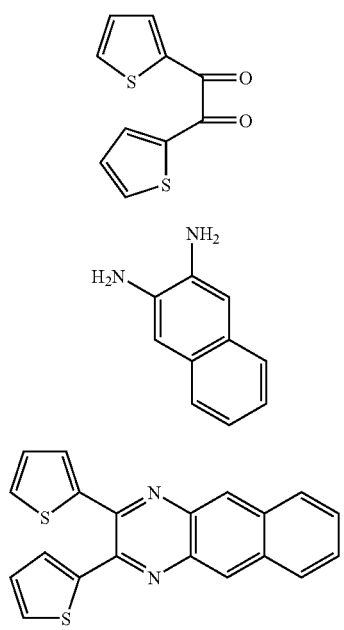

Synthesis Example 6

The reaction was carried out in accordance with the same procedures as those conducted in Synthesis Example 1 except that diketone shown in [formula 19] and diamine shown in [formula 12] were used. The obtained quinoxaline derivative is represented by [formula 20].

[formula 19]

[formula 12]

[formula 20]

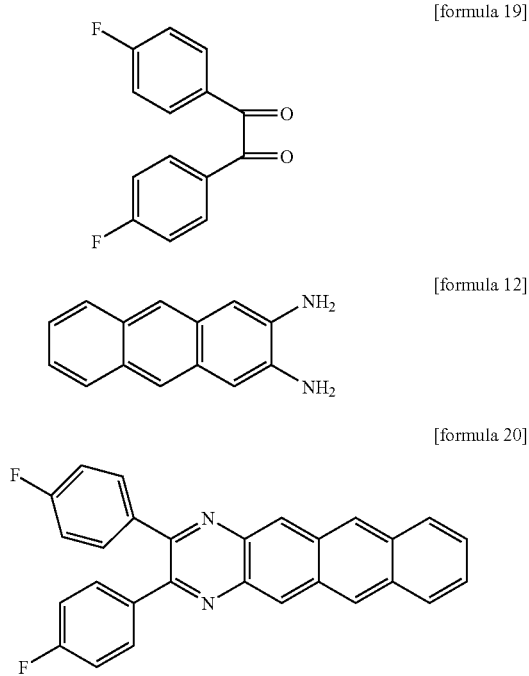

Synthesis Example 7

The reaction was carried out in accordance with the same procedures as those conducted in Synthesis Example 1 except that diketone shown in [formula 21] and diamine shown in [formula 15] were used. The obtained quinoxaline derivative is represented by [formula 22].

[formula 21]

[formula 15]

[formula 22]

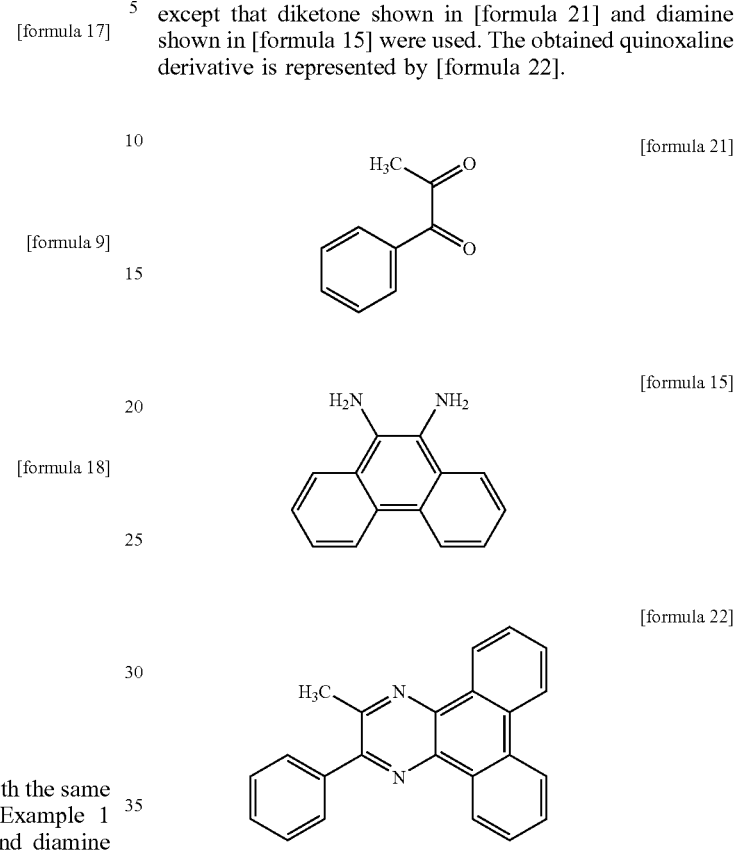

Synthesis Example 8

The reaction was carried out in accordance with the same procedures as those conducted in Synthesis Example 1 except that diketone shown in [formula 23] and diamine shown in [formula 9] were used. The obtained quinoxaline derivative is represented by [formula 24].

[formula 23]

[formula 9]

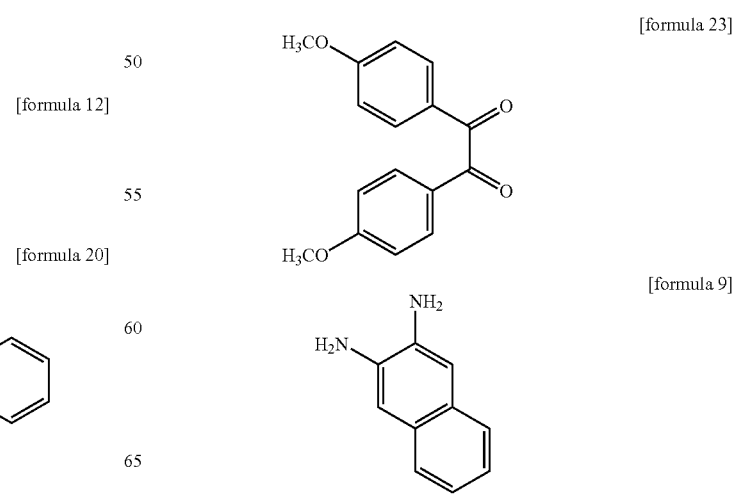

-continued

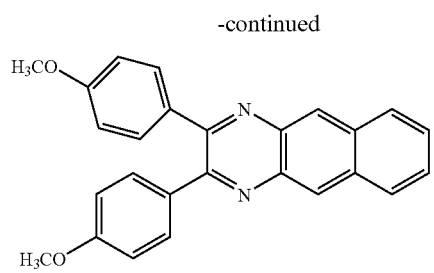
[formula 24]

Synthesis Example 9

The reaction was carried out in accordance with the same procedures as those conducted in Synthesis Example 1 except that diketone shown in [formula 25] and diamine shown in [formula 12] were used. The obtained quinoxaline derivative is represented by [formula 26].

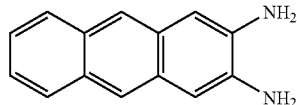
[formula 25]

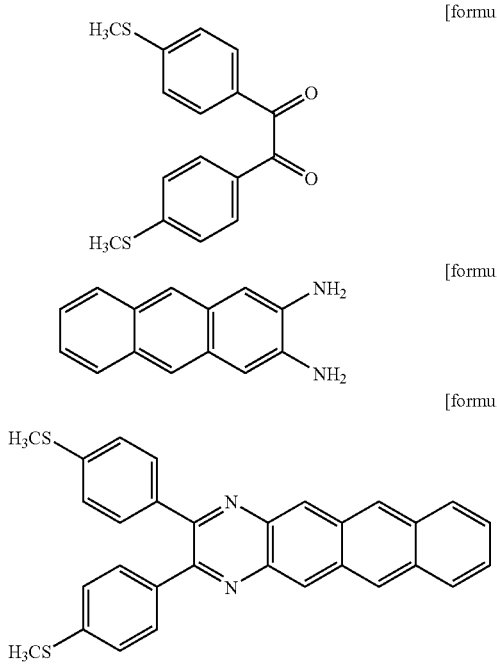
[formula 12]

[formula 26]

Synthesis Example 10

The reaction was carried out in accordance with the same procedures as those conducted in Synthesis Example 1 except that diketone shown in [formula 27] and diamine shown in [formula 15] were used. The obtained quinoxaline derivative is represented by [formula 28].

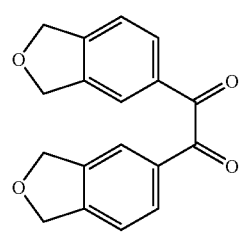
[formula 27]

-continued

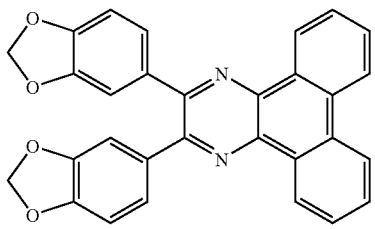
[formula 15]

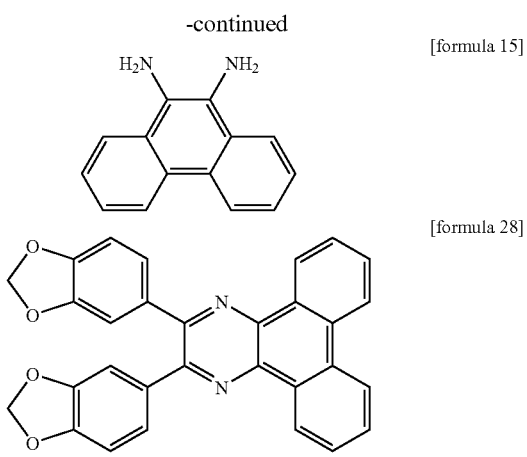
[formula 28]

Synthesis Example 11

The reaction was carried out in accordance with the same procedures as those conducted in Synthesis Example 1 except that diketone shown in [formula 29] and diamine shown in [formula 9] were used. The obtained quinoxaline derivative is represented by [formula 30].

[formula 29]

[formula 9]

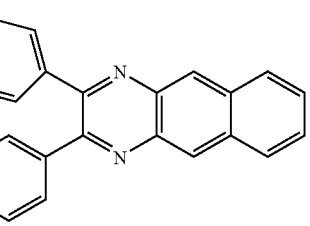
[formula 30]

Synthesis Example 12

The reaction was carried out in accordance with the same procedures as those conducted in Synthesis Example 1 except that diketone shown in [formula 31] and diamine shown in [formula 12] were used. The obtained quinoxaline derivative is represented by [formula 32].

[formula 31]

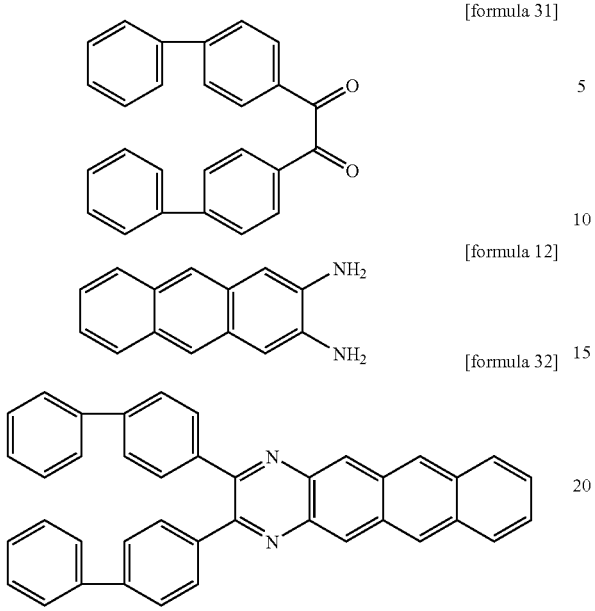

[formula 12]

[formula 32]

Synthesis Example 13

The reaction was carried out in accordance with the same procedures as those conducted in Synthesis Example 1 except that diketone shown in [formula 33] and diamine shown in [formula 15] were used. The obtained quinoxaline derivative is represented by [formula 34].

[formula 33]

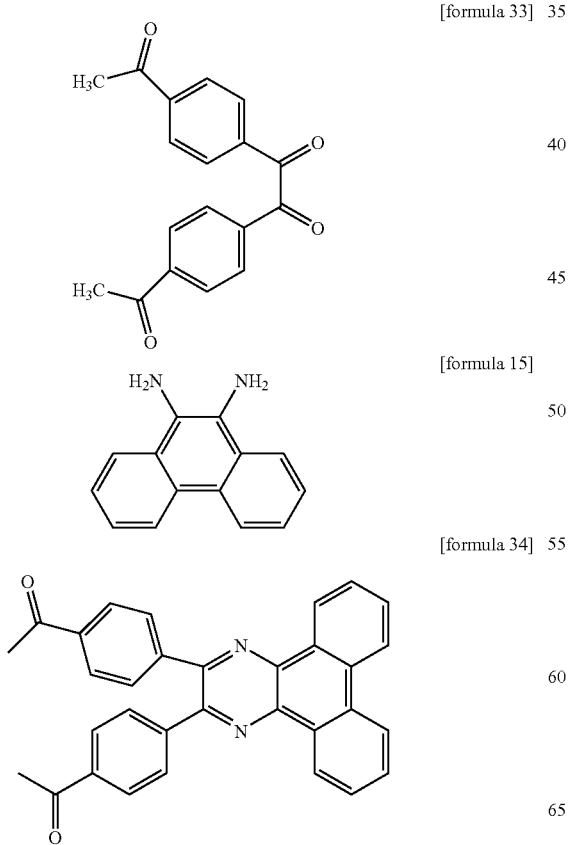

[formula 15]

[formula 34]

Synthesis Example 14

The reaction was carried out in accordance with the same procedures as those conducted in Synthesis Example 1 except that diketone shown in [formula 35] and diamine shown in [formula 9] were used. The obtained quinoxaline derivative is represented by [formula 36].

[formula 35]

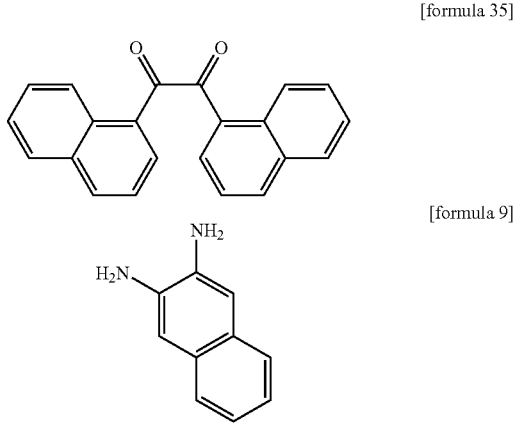

[formula 9]

[formula 36]

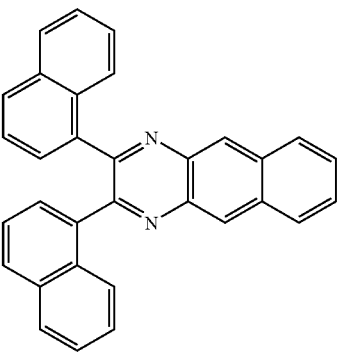

Synthesis Example 15

The reaction was carried out in accordance with the same procedures as those conducted in Synthesis Example 1 except that diketone shown in [formula 37] and diamine shown in [formula 12] were used. The obtained quinoxaline derivative is represented by [formula 38].

[formula 37]

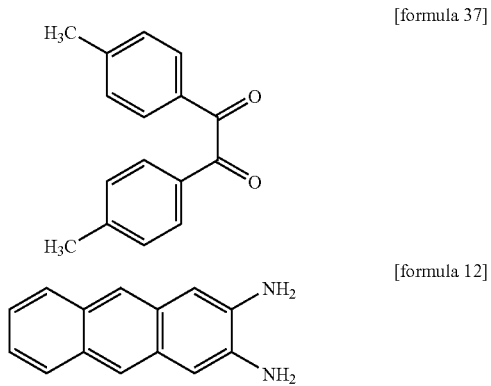

[formula 12]

-continued

[formula 38]

Synthesis Example 16

The reaction was carried out in accordance with the same procedures as those conducted in Synthesis Example 1 except that diketone shown in [formula 39] and diamine shown in [formula 40] were used. The obtained quinoxaline derivative is represented by [formula 41].

[formula 39]

[formula 40]

[formula 41]

Synthesis Example 17

The reaction was carried out in accordance with the same procedures as those conducted in Synthesis Example 1 except that diketone shown in [formula 42] and diamine shown in [formula 40] were used. The obtained quinoxaline derivative is represented by [formula 43].

[formula 42]

[formula 40]

[formula 43]

Synthesis Example 18

The reaction was carried out in accordance with the same procedures as those conducted in Synthesis Example 1 except that diketone shown in [formula 44] and diamine shown in [formula 40] were used. The obtained quinoxaline derivative is represented by [formula 45].

[formula 44]

[formula 40]

[formula 45]

Synthesis Example 19

The reaction was carried out in accordance with the same procedures as those conducted in Synthesis Example 1 except that diketone shown in [formula 46] and diamine shown in [formula 40] were used. The obtained quinoxaline derivative is represented by [formula 47].

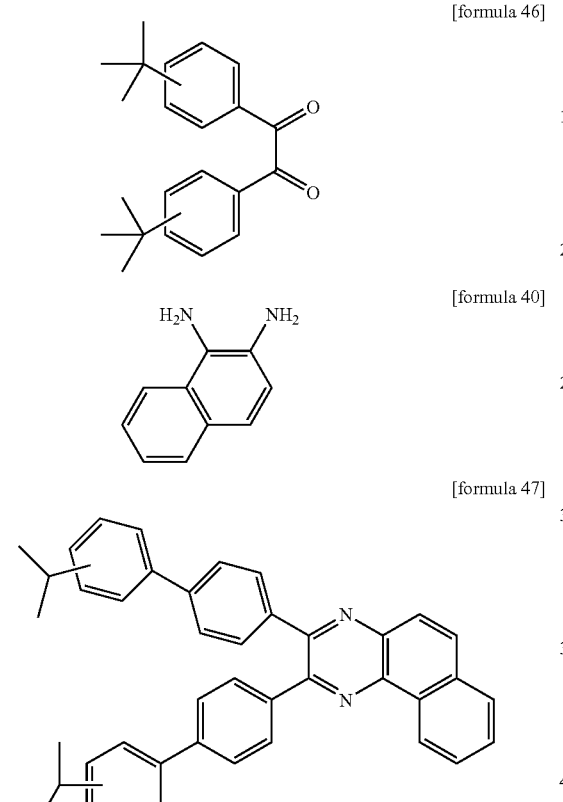

[formula 46]

[formula 40]

[formula 47]

Synthesis Example 20

The reaction was carried out in accordance with the same procedures as those conducted in Synthesis Example 1 except that diketone shown in [formula 48] and diamine shown in [formula 12] were used. The obtained quinoxaline derivative is represented by [formula 49].

[formula 48]

[formula 12]

[formula 49]

Synthesis Example 21

The reaction was carried out in accordance with the same procedures as those conducted in Synthesis Example 1 except that diketone shown in [formula 50] and diamine shown in [formula 15] were used. The obtained quinoxaline derivative is represented by [formula 51].

[formula 50]

[formula 15]

[formula 51]

Example 1

In this example, an electroluminescent device manufactured in such a way that a part of an electroluminescent layer is formed by quinoxaline derivatives according to the invention will be explained. A device configuration of an electroluminescent device formed over a substrate will be explained with reference to FIG. 1 in this example.

First, a first electrode 101 of an electroluminescent device is formed over a substrate 100. In this example, the first electrode 101 serves as an anode. The first electrode 101 is formed by ITO (indium tin oxide), which is a transparent conductive film, to have a thickness of 110 nm by sputtering. As the sputtering, bipolar sputtering, ion beam sputtering, facing targets sputtering, or the like can be used.

Next, an electroluminescent layer 102 is formed over the first electrode (anode) 101. This example will explain the case that the electroluminescent layer 102 is formed to have a lamination structure composed of a hole injecting layer 111, a hole transporting layer 112, a light-emitting layer 113, and an electron transporting layer 114; and that quinoxaline derivatives according to the invention is used for the electron transporting layer 114.

The hole injecting layer 111 is formed as the following procedures, that is, a substrate provided with the first electrode 101 is fixed to a substrate holder of a commercial vacuum vapor deposition system in such a way that the surface on which the first electrode 101 is formed is down; and copper phthalocyanine (hereinafter, Cu-Pc) is set in an evaporation source installed with inside of the vacuum vapor deposition system; then, the hole injecting layer 111 is formed to have a thickness of 20 nm by vapor deposition by resistance heating method.

Next, the hole transporting layer 112 is formed by a material having excellent hole transportation properties. Here, 4,4'-bis[N-(1-naphthyl)-N-phenyl-amino]-biphenyl (hereinafter, α-NPD) is deposited to have a thickness of 30 nm by the same method.

Next, the light-emitting layer 113 is formed. Hole-electron pairs are recombined within the light-emitting layer 113 to generate luminescence. Here, Alq$_3$ is deposited to have a thickness of 50 nm by the same method.

And the electron transporting layer 114 is formed. The electron transporting layer 114 is formed by quinoxaline derivatives according to the invention. As the quinoxaline derivatives, materials represented by synthesis examples 1-21 can be used; however, 2,3-Di-furan-2-yl-dibenzo[f,h]quinoxaline represented by Synthesis Example 1 is deposited to have a thickness of 20 nm by the same method.

As described above, after the electroluminescent layer 102 having a lamination structure is formed, a second electrode 103 which serves as a cathode is formed by sputtering or vapor deposition. In this example, the second electrode 103 can be formed over the electroluminescent layer 102 by depositing aluminum-lithium alloys (Al:Li) to have a thickness of 100 nm by sputtering.

Accordingly, an electroluminescent device can be formed by quinoxaline derivatives according to the invention. In this example, the first electrode is formed over the substrate by an anode material to serve as an anode; however, the invention is not limited thereto. The first electrode can be formed by a cathode material to serve as a cathode. In this case (in case of exchanging the anode for the cathode), the lamination sequence, which was used to form the electroluminescent layer in this example, is reversed. In addition, the first electrode (anode) is transparent to light in order to pass light generated in the electroluminescent layer through the first electrode (anode); however, the invention is not limited thereto. Light can pass through the second electrode (cathode) by forming the cathode by a material capable of keeping the transmittance.

As described in this example, an electron transporting layer which has excellent electron transportation and blocking properties can be formed by using quinoxaline derivatives according to the invention for forming the electron transporting layer so that an electroluminescent device which has excellent luminous efficiency and which operates at low voltage can be obtained.

Example 2

Figure 2:
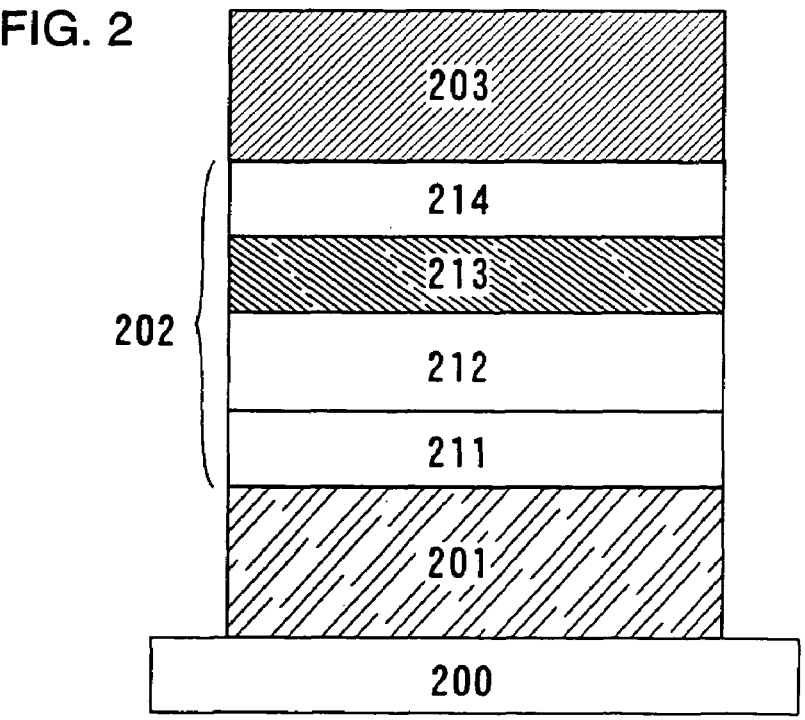
FIG. 2 is an explanatory view of a configuration of an electroluminescent device according to the invention.

In this example, an electroluminescent device which is formed in such a way that a part of an electroluminescent layer is formed by quinoxaline derivatives according to the invention in accordance with the procedures different from that described in the example 1 will be explained. Specifically, the case that quinoxaline derivatives according to the invention is used to form a light-emitting layer of an electroluminescent layer will be explained with reference to FIG. 2.

In a similar procedure as that conducted in the example 1, a first electrode 201 is formed, and an electroluminescent layer 202 is formed over the first electrode 201 by vapor deposition.

A hole injecting layer 211 is formed on the first electrode 201. As a material for forming the hole injecting layer 211, a known hole injecting material can be used. In this embodiment, the hole injecting layer 211 is formed by Cu-Pc to have a thickness of 20 run by vapor deposition.

Next, a hole transporting layer 212 is formed. As a material for forming the hole transporting layer 212, a known hole transporting material can be used. In this example, the hole transporting layer 212 is formed by α-NPD to have a thickness of 30 nm by vapor deposition.

Next, a light-emitting layer 213 is formed. In this embodiment, quinoxaline derivatives according to the invention (including materials represented by Synthesis Examples 1-21) can be used as a host material for forming the light-emitting layer 213, and a known light-emitting material can be used as a guest material for forming the light-emitting layer 213. Accordingly, the light-emitting layer 213 is formed to have a thickness of 30 nm by 2,3-Di-furan-2-yl-dibenzo[f,h]quinoxaline represented by Synthesis Example 1 among quinoxaline derivatives and perylene by co-evaporation.

Next, an electron transporting layer 214 is formed. As a material for forming the electron transporting layer 214, a known electron transporting material can be used. Specifically, BAlq, PBD, OXD-7, BCP, or the like can be used. In this example, the electron transporting layer 214 is formed to have a thickness of 20 nm by quinoxaline derivatives used for forming the light-emitting layer, in particular, 2,3-Di-furan-2-yl-dibenzo[f,h]quinoxaline by vapor deposition.

And after forming the electroluminescent layer 202 to have a lamination structure, a second electiode 203 is formed in accordance with the same procedures as those conducted in Example 1. Consequently, an electroluminescent device can be obtained.

As described in this example, it is extremely effective to use quinoxaline derivatives according to the invention as the host material for forming the light-emitting layer for increasing luminous efficiency, because the wide energy gap of quinoxaline derivatives can be utilized effectively.

Example 3

In this embodiment, the way in which a light-emitting layer is formed by quinoxaline derivatives according to the invention and a configuration is different from that explained in Example 2 will be explained. In this configuration, structures except both a light-emitting layer and an electron transporting layer are the same as those described in the example 2 and will not be further explained in this example.

Figure 3:
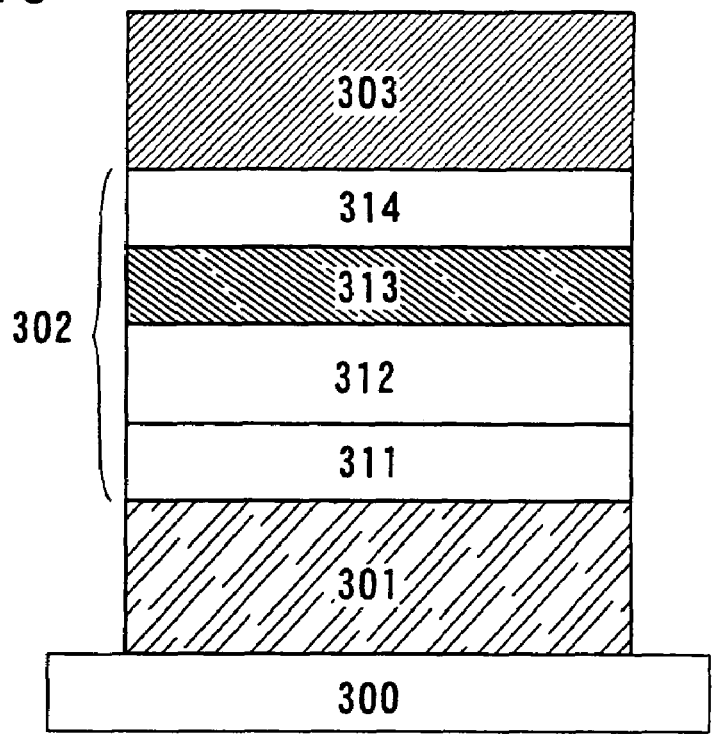
FIG. 3 is an explanatory view of a configuration of an electroluminescent device according to the invention.

In this example, quinoxaline derivatives according to the present invention is used as a guest material in this example for forming a light-emitting layer 313 which is one component of the electroluminescent layer 302 interposed between the first electrode 301 and a second electrode 302 as shown in FIG. 3. As the quinoxaline derivatives, a material represented by Synthesis Examples 1-21 can be used.

The light-emitting layer 313 can be formed by co-evaporation of the quinoxaline derivatives and CBP serving as host materials. As the host material, a known material can be used. Specifically, TPD, α-NPD, TCTA, PBD, OXD-7, BCP, or the like can be used.

The quinoxaline derivatives according to the invention can be used as a guest material for blue light emission in terms of having wide energy gap and achieving phosphorescent wavelength around 450 nm. In addition, it is known that the quinoxaline derivatives according to the invention are materials having electron transportation properties. It is also generally known that membrane resistance is reduced by using materials having carrier transportation properties as a guest material. (Refer to Nikkei Business Publications., Inc. "45$^{th}$ NIKKEI MICRODEVICES Seminar, Leading Edge of Organic EL" NIKKEI MICRODEVICES, pp.3.1-3.12 [Reference 6].) Therefore, a driving voltage can be reduced by using quinoxaline derivatives according to the invention as a guest material for forming a light-emitting layer as described in this example.

Example 4

Figure 4:
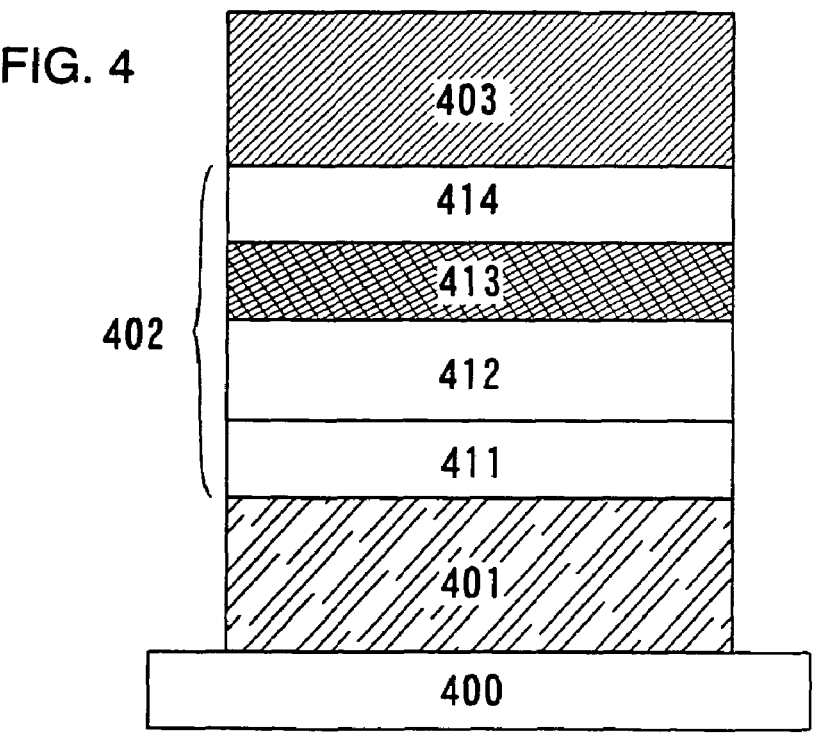
FIG. 4 is an explanatory view of a configuration of an electroluminescent device according to the invention.

In this example, an electroluminescent device that is formed in such a way that a part of an electroluminescent layer is formed by quinoxaline derivatives according to the invention having a different structure from that described in the example 1 will be explained. Specifically, the case that quinoxaline derivatives are used for forming a hole blocking layer of an electroluminescent layer will be explained with reference to FIG. 4.

A first electrode 401 is formed in accordance with the same procedures conducted in Example 1. An electroluminescent layer 402 is formed over the first electrode 401 by vapor deposition.

A hole injecting layer 411 is formed on the first electrode 401. As a material for forming the hole injecting layer 411, a known hole injecting material can be used. In this example, the hole injecting layer 411 is formed to have a thickness of 20 nm by Cu-Pc by vapor deposition.

Next, a light-emitting layer 412 is formed. As a material for forming the light-emitting layer 412, a known light-emitting material can be used. In this example, the light-emitting layer 412 is formed to have a thickness of 30 nm by α-NPD by vapor deposition.

Next, a hole blocking layer 413 is formed. The hole blocking layer 413 is formed by the quinoxaline derivatives according to the invention. As the quinoxaline derivatives, materials represented by Synthesis Examples 1-21 can be used. In this example, 2,3-Di-furan-2-yl-dibenzo[f,h]quinoxaline represented by Synthesis Example 1 is deposited by the same method to have a thickness of 20 nm.

Next, an electron transporting layer 414 is formed. As a materiaf for forming the electron transporting layer 414, a known electron transporting material can be used. In this example, the electron transporting layer 414 is formed to have a thickness of 30 nm by Alq$_3$ by vapor deposition.

And after forming the electroluminescent layer 402 to have a lamination structure, a second electrode 403 is formed in accordance with the same procedures as those conducted in Example 1. Consequently, an electroluminescent device can be obtained.

As described in this example, luminous efficiency can be improved by forming the hole blocking layer 413 by quinoxaline derivatives according to the invention because holes can be trapped in the light-emitting layer 412.

Example 5

Figure 5:
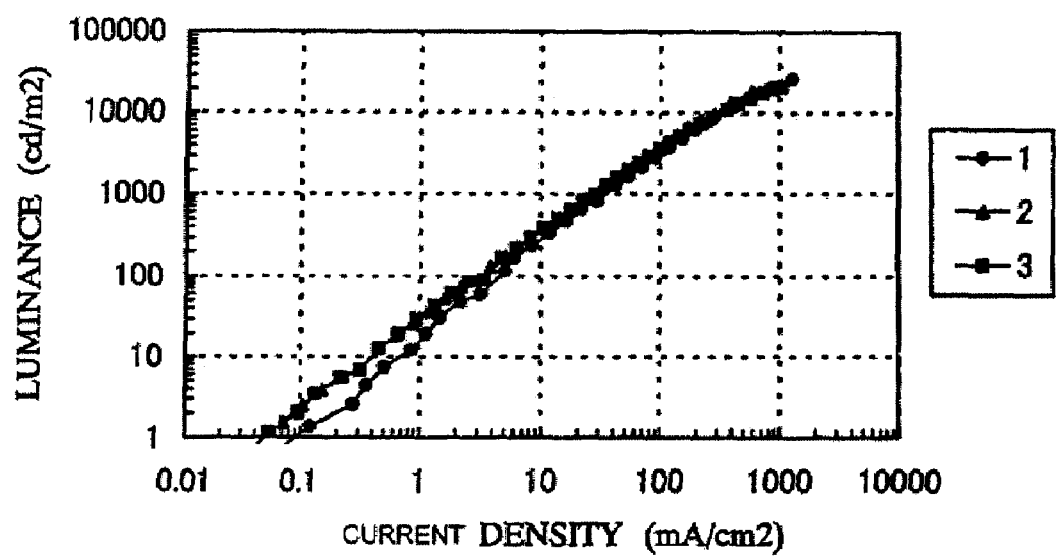
FIG. 5 is a graph showing device characteristics of an electroluminescent device.

Device characteristics of an electroluminescent device having the configuration described in Example 1: ITO/Cu-Pc (20 nm)/α-NPD (30 nm)/Alq$_3$ (30 nm)/FuQn (20 nm)/CaF (1 nm)/Al was measured. The measurement results will be explained in this example. As quinoxaline derivatives (FuQn) in this example, 2,3-Di-furan-2-yl-dibenzo[f,h]quinoxaline represented by Synthesis Example 1 is used. Plot 3 in FIGS. 5 to 8 is shown for the measurement results. The luminance-current density plot 3 in FIG. 5 shows that a luminance of approximately 4000 cd/m$^2$ can be achieved at current density of 100 mA/cm$^2$.

Figure 6:
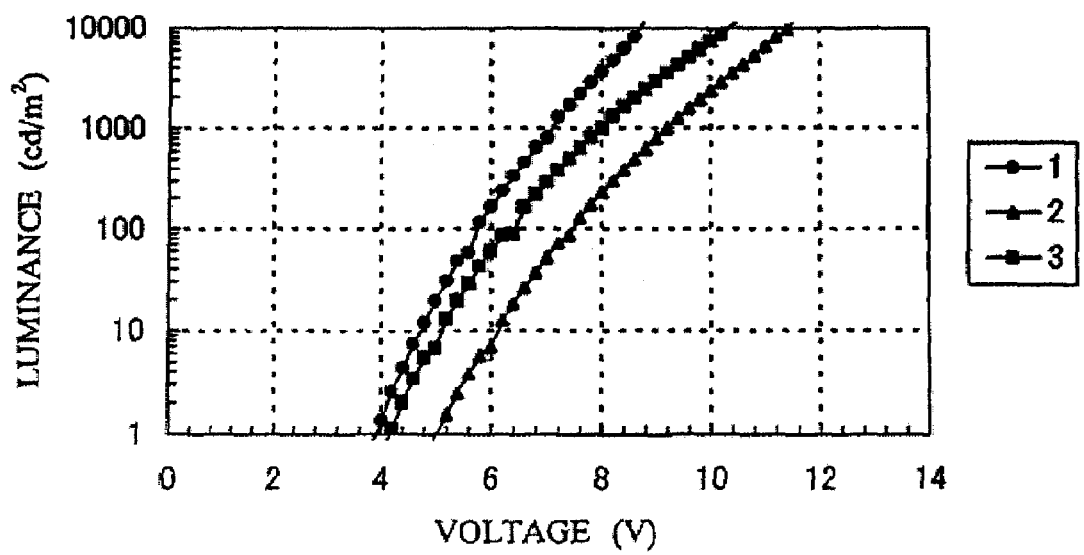
FIG. 6 is a graph showing device characteristics of an electroluminescent device.

The luminance-voltage plot 3 in FIG. 6 shows that a luminance of approximately 1000 cd/m$^2$ can be achieved at an applied voltage of 8 V.

Figure 7:
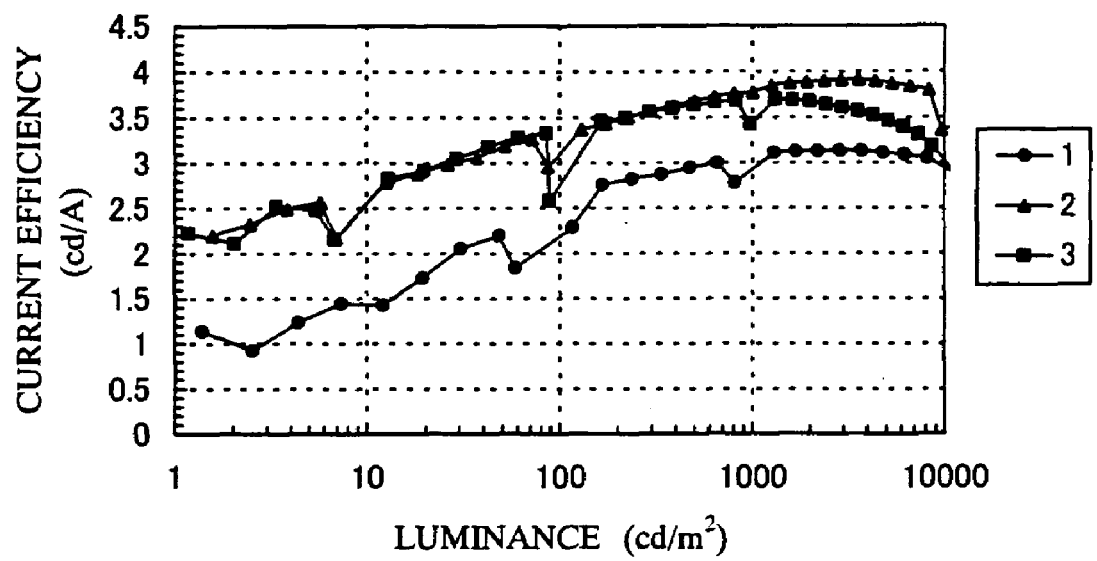
FIG. 7 is a graph showing device characteristics of an electroluminescent device.

The current efficiency-luminance plot 3 in FIG. 7 shows that approximately a current efficiency of 2.8 cd/A is obtained at a luminance of 100 cd/m$^2$.

Figure 8:
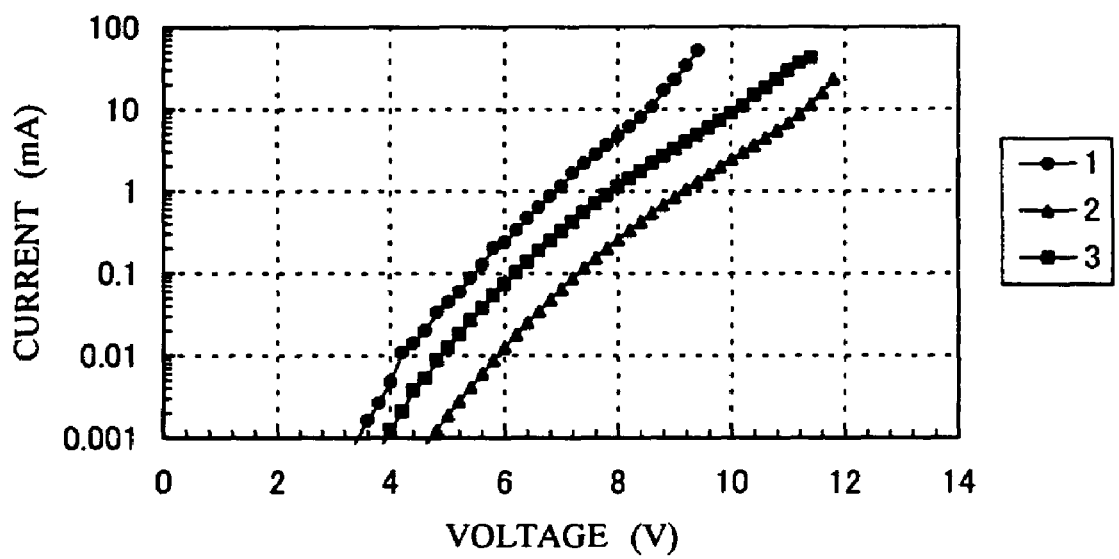
FIG. 8 is a graph showing device characteristics of an electroluminescent device.

Further, the current-voltage plot 3 in FIG. 8 shows that the current flow is approximately 0.4 mA at an applied voltage of 7 V.

Comparative Example 1

Device characteristics of an electroluminescent device having the configuration: ITO/Cu-Pc (20 nm)/α-NPD (30 nm)/Alq$_3$ (30 nm)/CaF (1 nm)/Al, in which an electron transporting layer formed by quinoxaline derivatives is not included which is different from the device measured in Example 5 was measured. Plot 1 in FIGS. 5 to 8 is shown for the measurement results. The luminance-current plot 1 in FIG. 5 shows that a luminance of approximately 4000 cd/m$^2$ can be achieved at the current density of 100 mA/cm$^2$. The luminance-current characteristics are similar to those of the device measured in Example 5.

The luminance-voltage plot 1 in FIG. 6 shows that a luminance of approximately 6000 cd/m$^2$ can be achieved at an applied voltage of 8 V. In this instance, the luminance with the applied current is improved which is largely caused by the fact that the overall thickness of the electroluminescent layer can be formed to be thin since the electroluminescent layer does not have an electron transporting layer. Therefore, it should not be understood that the electroluminescent device in this instance has better characteristics than those of the electroluminescent device described in Example 2.

In addition, the current efficiency-luminance plot 1 in FIG. 7 shows that a current efficiency of approximately 2.2 cd/A is obtained at a luminance of 100 cd/m$^2$. Therefore, the current efficiency of the device in this instance is worse than that of the device in Example 2. Judging from the result, the device in Example 2 has high luminance efficiency, which is caused by the fact that quinoxaline derivatives for forming the electron transporting layer has high hole blocking properties to trap holes in the light-emitting layer.

The current-voltage plot 1 in FIG. 8 shows that current flow is approximately 1 mA at an applied voltage of 7 V. As in the case with FIG. 6, it should not be understood that the electroluminescent device having this structure has better characteristics than those of the electroluminescent device in Example 2 since the amounts of current flow are depending on the thickness of an electroluminescent device.

Comparative Example 2

Device characteristics of an electroluminescent device in Example 5 having the configuration: ITO/Cu-Pc (20 nm)/ α-NPD (30 nm)/Alq$_3$ (30 nm)/BCP (20 nm)/CaF (1 nm)/Al, in which an electron transporting layer is formed by bathocuproin (hereinafter, BCP), which has been conventionally used as a blocking material, instead of quinoxaline derivatives according to the present invention was measured. Plot 2 in FIGS. 5 to 8 is shown for the measurement results. The luminance-current plot 2 in FIG. 5 shows that a luminance of approximately 4000 cd/m$^2$ can be achieved at the current density of 100 mA/cm$^2$. The luminance-current characteristics are similar to those of the device measured in Example 5.

The luminance-voltage plot 2 in FIG. 6 shows that a luminance of approximately 200 cd/m$^2$ is only obtained at an applied voltage of 8 V. Therefore, the characteristics of the device using bathocuproin are inferior in electron transportation properties to the electroluminescent device having an electron transporting layer formed by quinoxaline derivatives according to the invention.

The current efficiency-luminance plot 2 in FIG. 7 shows that a current efficiency of approximately 3.1 cd/A is obtained at a luminance of 100 cd/m$^2$. As a whole, the characteristics of the electroluminescent device in this instance is very similar to those of the electroluminescent device in which the electron transporting layer is formed by quinoxaline derivatives according to the invention. Therefore, the current efficiency-luminance characteristics shows that quinoxaline derivatives according to the invention can maintain almost the same level of blocking properties as those of the conventional BCP.

Further, the current-voltage plot 2 in FIG. 8 shows that a current flow is approximately 0.08 mA at an applied voltage of 7 V. By the fact that electroluminescent device containing quinoxaline derivatives is superior in current-voltage characteristics to the electroluminescent device containing BCP, each of which has the same thickness, it can be considered that electron injection transportation properties of the electroluminescent device are improved by using quinoxaline derivatives.

Example 6

Figure 10A:
FIGS. 10A and 10B are photographs of the surfaces of quinoxaline derivatives according to the invention and a BCP thin film.

The state of the film surface of a thin film formed by quinoxaline derivatives according to the invention will be explained. FIG. 10A shows a sample which is composed of a thin film formed by depositing quinoxaline derivatives to have a thickness of 50 nm over a substrate, and which is sealed by a sealing substrate. The thin film of quinoxaline derivatives is a stable film without being crystallized the surface thereof.

Comparative Example 3

Figure 10B:
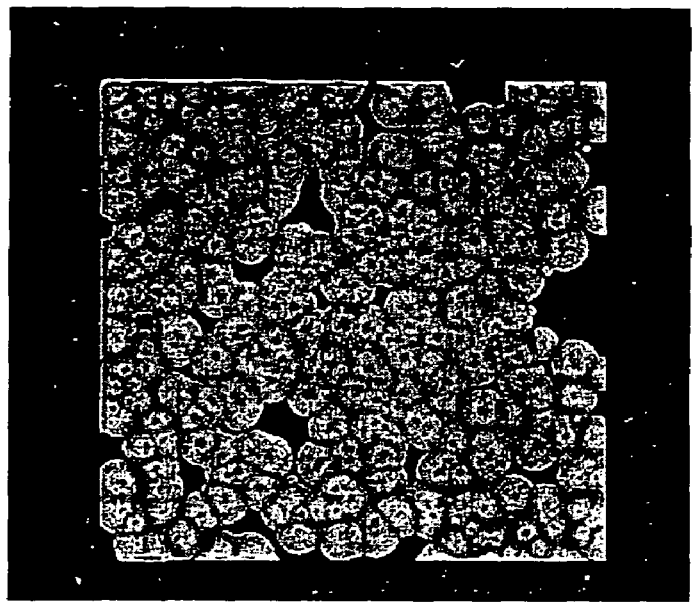

A sample is manufactured in accordance with the same procedures conducted in Example 6 except that a thin film of BCP is formed instead of forming a thin film of quinoxaline derivatives. As a result, the thin film of BCP is crystallized over time as shown in FIG. 10B.

The invention claimed is:

1. An electroluminescent device comprising a light-emitting layer comprising a quinoxaline derivative represented by:

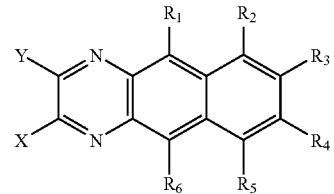

wherein X represents an unsubstituted aryl group or a substituted or unsubstituted heterocyclic group;

Y represents an unsubstituted aryl group, or a substituted or unsubstituted heterocyclic group, and R1 to R6 individually represent hydrogen, an alkyl group, an alkoxyl group, a substituted or unsubstituted aryl group, and a substituted or unsubstituted heterocyclic group.

2. An electroluminescent device comprising a light-emitting layer comprising a quinoxaline derivative represented by:

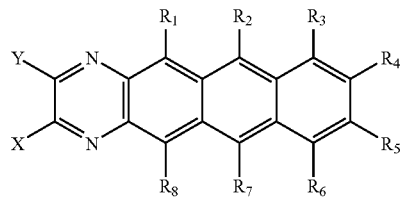

wherein X and Y individually represent an alkyl group, a substituted or unsubstituted aryl group, or a substituted or unsubstituted heterocyclic group, and R1 to R8 individually represent hydrogen, an alkyl group, an alkoxyl group, a substituted or unsubstituted aryl group, and a substituted or unsubstituted heterocyclic group.

3. An electroluminescent device comprising a light-emitting layer comprising a quinoxaline derivative represented by:

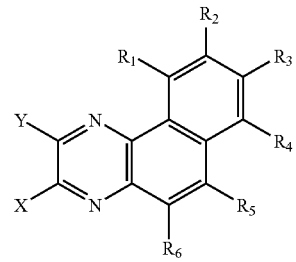

wherein X represents an alkyl group, an unsubstituted aryl group or a substituted or unsubstituted heterocyclic group;

Y represents an alkyl group, an unsubstituted aryl group, or a substituted or unsubstituted heterocyclic group, and R1 to R6 individually represent hydrogen, an alkyl group, an alkoxyl group, a substituted or unsubstituted aryl group, and a substituted or unsubstituted heterocyclic group.

4. An electroluminescent device comprising a light-emitting layer comprising a quinoxaline derivative represented by:

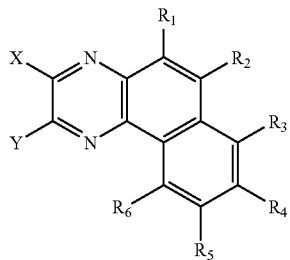

wherein X represents an alkyl group, an unsubstituted aryl group or a substituted or unsubstituted heterocyclic group;
Y represents an alkyl group, an unsubstituted aryl group, or a substituted or unsubstituted heterocyclic group, and
R1 to R6 individually represent hydrogen, an alkyl group, an alkoxyl group, a substituted or unsubstituted aryl group, and a substituted or unsubstituted heterocyclic group.

5. An electroluminescent device comprising a light-emitting layer comprising a quinoxaline derivative represented by:

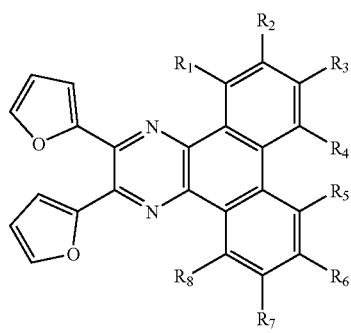

wherein
R1 to R8 individually represent hydrogen, an alkyl group, an alkoxyl, group, a substituted or unsubstituted aryl group, and a substituted or unsubstituted heterocyclic group.

6. The electroluminescent device according to claim 1, wherein the quinoxaline derivative comprises a heterocyclic group represented by:

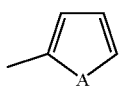

wherein A represents S or O.

7. The electroluminescent device according to claim 1, wherein the ligh-emitting layer further comprises a phosphorescent material as a guest material.

8. The electroluminescent device according to claim 2, wherein the quinoxaline derivative comprises a heterocyclic group represented by:

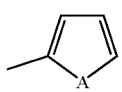

wherein A represents S or O.

9. The electroluminescent device according to claim 2, wherein the light-emitting layer further comprises a phosphorescent material as a guest material.

10. The electroluminescent device according to claim 3, wherein the quinoxaline derivative comprises a heterocyclic group represented by:

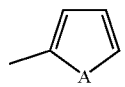

wherein A represents S or O.

11. The electroluminescent device according to claim 3, wherein the light-emitting layer further comprises a phosphorescent material as a guest material.

12. The electroluminescent device according to claim 4, wherein the quinoxaline derivative comprises a heterocyclic group represented by:

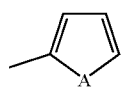

wherein A represents S or O.

13. The electroluminescent device according to claim 4, wherein the light-emitting layer further comprises a phosphorescent material as a guest material.

14. The electroluminescent device according to claim 5, wherein the light-emitting layer further comprises a phosphorescent material as a guest material.

15. An electroluminescent device comprising a light-emitting layer comprising a quinoxaline derivative represented by:

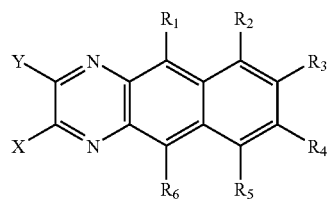

wherein each of X and Y represents an alkyl group,
R1 to R6 individually represent hydrogen, an alkyl group, an alkoxyl group, a substituted or unsubstituted aryl group, and a substituted or unsubstituted heterocyclic group.

16. The electroluminescent device according to claim 15, wherein the quinoxaline derivative comprises a heterocyclic group represented by:

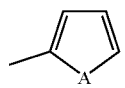

wherein A represents S or O.

17. The electroluminescent device according to claim 16, wherein the light-emitting layer further comprises a phosphorescent material as a guest material.

* * * * *